United States Patent
Bertholdt

(10) Patent No.: US 8,993,324 B2
(45) Date of Patent: Mar. 31, 2015

(54) PROCESS AND SUPPORT STRUCTURE FOR THE CULTIVATION OF LIVING CELLS

(75) Inventor: Günter Bertholdt, Heiningen (DE)

(73) Assignee: Bioregeneration GmbH, Garching (DE)

( * ) Notice: Subject to any disclaimer, the term of this patent is extended or adjusted under 35 U.S.C. 154(b) by 1072 days.

(21) Appl. No.: 12/526,752

(22) PCT Filed: Feb. 12, 2008

(86) PCT No.: PCT/EP2008/051692
§ 371 (c)(1),
(2), (4) Date: Aug. 11, 2009

(87) PCT Pub. No.: WO2008/098942
PCT Pub. Date: Aug. 21, 2008

(65) Prior Publication Data
US 2010/0041148 A1 Feb. 18, 2010

(30) Foreign Application Priority Data
Feb. 12, 2007 (DE) .......................... 10 2007 006 843

(51) Int. Cl.
| | |
|---|---|
| C12N 5/071 | (2010.01) |
| B29C 33/44 | (2006.01) |
| B28B 7/34 | (2006.01) |
| C12N 5/00 | (2006.01) |
| C08L 1/04 | (2006.01) |
| C12P 19/04 | (2006.01) |

(52) U.S. Cl.
CPC ............... C12N 5/0068 (2013.01); C08L 1/04 (2013.01); C12P 19/04 (2013.01); C12N 2533/78 (2013.01)
USPC ...................................................... 435/395

(58) Field of Classification Search
None
See application file for complete search history.

(56) References Cited

U.S. PATENT DOCUMENTS

| | | | |
|---|---|---|---|
| 2003/0013163 A1 | 1/2003 | Klemm et al. | |
| 2004/0147018 A1 | 7/2004 | Haverich et al. | |

FOREIGN PATENT DOCUMENTS

| | | | |
|---|---|---|---|
| DE | 4123660 A1 | 1/1993 | |
| DE | 10061704 A1 | 6/2002 | |
| DE | 10361898 A1 | 7/2005 | |
| EP | 0186495 A2 | 7/1986 | |
| EP | 0396344 | 11/1990 | |
| EP | 0420171 A1 | 4/1991 | |
| EP | 0451706 A1 | 10/1991 | |
| EP | 0531733 A1 | 3/1993 | |
| EP | 1230939 | 8/2002 | |
| EP | 1569578 B1 * | 11/2007 | ............... A61F 2/86 |
| JP | 2006325534 A | 12/2006 | |
| WO | WO-0161026 | 8/2001 | |
| WO | WO-03020191 A1 | 3/2003 | |
| WO | WO-03070084 | 8/2003 | |
| WO | WO-2006042267 A2 | 4/2006 | |
| WO | WO-2007093445 A1 | 8/2007 | |

OTHER PUBLICATIONS

Ma et al., Biodegradable Polymer Scaffolds with Well-Defined Interconnected Spherical Pore Network, 2001, Tissue Engineering 7(1): 23-33.*
Hacker et al., Towards biomimetic scaffolds: Anhydrous scaffold fabrication from biodegradable amine-reactive diblock copolymers, 2003, Biomaterials 24: 4459-4473.*
Iwahori, T. et al, "Radial Flow Bioreactor for the Creation of Bioartificial Liver and Kidney", 2005 Transplantation Proceedings, 37 (pp. 212-214).
Translation of Russian Search Report for corresponding Application No. 2009134114 (2 pgs.).
European Search Report for corresponding EP Application No. EP 10 15 7287 dated May 4, 2010 (12 pgs.).
Backdahl, et al. Mechanical properties of bacterial cellulose and interactions with smooth muscle cells. Biomaterials, 2006, vol. 27, No. 9, pp. 2141-2149.
Bodin, Aase, et al. Influence of cultivation conditions on mechanical and morphological properties of bacterial cellulose tubes. Biotechnology and Bioengineerings, Wiley & Sons, 2006. vol. 97, No. 2. pp. 425-434.
Muller, et al. Cellulose-based scaffold materials for cartilage tissue engineering. Biomaterials, 2006, vol. 27, No. 21, pp. 3955-3963.
Svensson, A., et al. Bacterial cellulose as a potential scaffold for tissue engineering of cartilage. Biomaterials, 2005, vol. 26, No. 4, pp. 419-431.
International Search Report of the International Searching Authority for PCT/EP2008/051692 mailed Nov. 17, 2008 (5 pages).

* cited by examiner

Primary Examiner — Robert Yamasaki
(74) Attorney, Agent, or Firm — Harris Beach PLLC

(57) ABSTRACT

In a process for the cultivation of living cells, in which the cells are cultivated on a support structure (14), the support structure (14) comprises cellulose. A process for the production of a support structure (14) of cellulose for the cultivation of living cells comprises the steps: preparation of a hollow mould; cultivation of cellulose-forming organisms in an interior space formed by the hollow mould, in order to allow the support structure (14) to grow in the interior space; demoulding of the hollow mould. In the step of demoulding the hollow mould, at least part (2, 3, 4) of the hollow mould is irreversibly deformed.

7 Claims, 4 Drawing Sheets

1

PROCESS AND SUPPORT STRUCTURE FOR THE CULTIVATION OF LIVING CELLS

This application is a national stage application under 35 U.S.C. §371 of PCT Application No. PCT/EP2008/051692 filed Feb. 12, 2008, which claims priority to and the benefit of German patent application Serial No. 10 2007 006 843.5, filed Feb. 12, 2007, which is incorporated herein by reference in its entirety.

BACKGROUND OF THE INVENTION

The invention relates to a process for the cultivation of living cells in which the cells are cultivated on a support structure (14) and to the use of a structure comprising crystalline cellulose. The invention relates further to a process for the production of a support structure (14) of cellulose for the cultivation of living cells, comprising the steps:
preparation of a hollow mould;
cultivation of cellulose-forming organisms in an interior space formed by the hollow mould, in order to allow the support structure to grow in the interior space;
demoulding of the hollow mould; to a support structure (14) for the cultivation of living cells, to a support structure (14) for the cultivation of living cells, having at least one tubular void (15) which branches in at least one location, wherein at least some of the branches converge again in a different location, to a support structure (14) for the cultivation of living cells, having in its inside a plurality of voids which are separate from one another, and to a hollow mould for the preparation of a support structure (14) comprising crystalline cellulose for the cultivation of living cells.

PRIOR ART

It is frequently desirable to culture living cells in vitro, for example from cells which have been taken from an organism, in order to implant the cultured cells in the same organism and thus obtain or restore a tissue function. The culturing of cells or cell tissues in vitro is frequently also referred to as "tissue engineering". The tissues are preferably soft tissue, for example skin, muscle or fatty tissue, as opposed to hard tissue or bone tissue.

It is known to cultivate living cells in culture vessels, for example culture bottles or culture dishes, where, covered by the nutrient medium, they form a single-layer ("two-dimensional") cell layer on the base of the culture vessel. However, the cells so cultivated can differ in terms of their properties from cells of the same type that are found in vivo in a tissue unit within an organism, which can substantially impair their diagnostic and therapeutic value.

A living tissue generally consists of a large number of specialised cells which influence one another with the aid of signal molecules, and it is supposed that cells orient themselves within concentration gradients of small-molecular substances and are able to behave in a particular way. The term "positional information" is also used here. Between the cells of a tissue there are support structures, called the extracellular matrix, which consist of macromolecules released by the cells and which stabilise the cells in their respective positions. If the extracellular matrix is destroyed and the cells are mixed up, normal, differentiated somatic cells are no longer capable of rearranging themselves and rebuilding the lost structures. It has been found, however, that these cells can resume their normal function if they are brought into their original spatial relationship with the appropriate adjacent cells.

A known approach tries to recreate the extracellular matrix by cultivating cells "three-dimensionally" within special support structures also known as scaffolds. Scaffolds are at least foam-like, porous structures having a large inside surface area.

Scaffolds of biodegradable ("resorbable") materials are known. These are said, inter alia, to enable the cells growing in the scaffold gradually to replace the scaffold by their own extracellular matrix.

US Published Patent Application US 2005/0063939 A1 describes a scaffold suitable for tissue engineering which comprises a biodegradable, elastomeric polymer containing citric acid. European Patent Specification EP 1 053 757 B1 describes a carrier material of collagen (gelatin). International Published Patent Application WO 2006/099137 A1 describes a scaffold for wound healing comprising crosslinked fibrin and/or albumin. International Published Patent Application WO 2002/062961 discloses the production of scaffolds from peptides which arrange themselves into larger units ("self-assembling" peptides) in order to encapsulate cells.

A possible disadvantage of the use of resorbable materials is that they decompose too rapidly to ensure the necessary mechanical stability. In particular, there can be the risk that vessels produced with the aid of resorbable scaffolds will not carry blood reliably. A further possible disadvantage is that residual material remains, which initiates foreign body or rejection reactions. For these and other reasons, scaffolds of non-resorbable materials have also been proposed.

Specification WO 03/070084 describes a tubular scaffold for the regeneration of blood vessels from non-resorbable fibers such as nylon, SILASTIC™, silicone, polyurethane and polyester. International Published Patent Application WO 2006/096791 discloses the use of numerous resorbable and non-resorbable synthetic polymers that are available at present to produce so-called nanofilaments, from which a coated scaffold is to be constructed. It can be a disadvantage of non-resorbable materials that they initiate at least slight tissue reactions. In addition, it is possible that the materials will be attacked and destroyed in the case of a longer implantation time in the body.

When cultivating cells or tissues in vitro, it can be necessary to take measures to supply nutrients and/or oxygen to the cells. In European Published Patent Application EP 1 230 939 A1 there is described a primary vascularised tissue matrix prepared from parts of the gastrointestinal tract of the pig. During the preparation it is to be ensured that a complete vascular branch with incoming artery and outgoing vein is present. When the animal cells have been removed by so-called acellularisation processes, the resulting matrix is to be perfused with blood and populated with human cells. In this manner it is said to be possible to supply even a relatively large number of cells and greater layer thicknesses with sufficient nutrients, minerals and oxygen. A possible disadvantage, however, is that the matrix used contains considerable amounts of animal protein and other potentially immunogenic molecules. A further possible disadvantage is that the animal origin of the matrix makes the process more difficult to standardise.

International Published Patent Application WO 2006/042287 A2 discloses a multi-layer scaffold with microchannels for use in tissue engineering, which scaffold is coated with bacterial cellulose. However, the scaffold described therein is optimised essentially for the culturing of cartilage tissue and has only limited suitability for implantation. In particular, it is not clear how coating with bacterial cellulose is to be effected, because the mentioned procedure does not lead to a uniform layer, nor does it indicate how the layer is to adhere to the substrate.

International Published Patent Application WO 2001/61026 A1 discloses a process for the production of a hollow body of microcrystalline cellulose of bacterial origin, which hollow body is said to be implantable into the carotid artery of a rat without any adverse effect such as foreign body reaction or thrombosis. However, the process described therein is only suitable for producing a hollow body having a length of about 20 millimeters.

Problem Underlying the Invention

The object underlying the invention is to provide an improved process for the cultivation of living cells. An additional object underlying the invention is to provide a novel use of a structure comprising crystalline cellulose. A further object underlying the invention is to provide an improved process for the production of a support structure comprising crystalline cellulose, an improved support structure for the cultivation of living cells, and an improved hollow mould for the production of a support structure comprising crystalline cellulose.

Solution According to the Invention

In order to achieve the object, the invention teaches a process for the cultivation of living cells in which the cells are cultivated on a support structure (14), characterised in that the support structure (14) comprises crystalline cellulose, the use of a support structure (14), comprising crystalline cellulose, on which cells are cultivated, a process for the production of a support structure (14) comprising crystalline cellulose for the cultivation of living cells, comprising the steps:
preparation of a hollow mould;
cultivation of cellulose-forming organisms in an interior space formed by the hollow mould, in order to allow the support structure to grow in the interior space;
demoulding of the hollow mould;
characterised in that at least part (2, 3, 4) of the hollow mould is irreversibly deformed in the step of demoulding the hollow mould,
a support structure (14) for the cultivation of living cells, a support structure (14) for the cultivation of living cells, having at least one tubular void (15) which branches in at least one location, wherein at least some of the branches converge again in a different location, characterised in that the support structure (14) comprises crystalline cellulose, and a support structure (14) for the cultivation of living cells, having in its inside a plurality of voids which are separate from one another, characterised in that the support structure (14) comprises crystalline cellulose, and a hollow mould for the production of a support structure (14) comprising crystalline cellulose for the cultivation of living cells, characterised in that it comprises a mould core (2, 3, 4, 5) which is formed at least partially of polyvinyl alcohol and/or summer wax.

The support structure according to the invention can be used in the cultivation of cells advantageously as a replacement for an extracellular matrix.

It is an aspect of the present invention that it uses the advantageous properties of crystalline cellulose, preferably microcrystalline cellulose in natural form, such as microcrystalline cellulose produced by the bacterium *Acetobacter xylinum*, in the preparation of support structures for the cultivation of living cells.

It is an achievable advantage of the invention that the support structures are non-toxic and non-immunogenic. In particular, it is possible for the support structures not to initiate a foreign body or immune reaction, or to initiate only a reduced foreign body or immune reaction, even after implantation in an organism, for example in the human organism.

It is a further achievable advantage of the invention that the support structures are not resorbed. It is thereby possible to ensure in particular greater mechanical stability during the cultivation of the cells or even over the prolonged period thereafter.

It is an achievable advantage that the support structure, although it is not resorbed, does not interfere, or interferes less, with the cultivation of the cells, both in vitro and in vivo, in particular because a structure having a low cellulose content can already ensure high stability and the remainder of the support structure can consist substantially of water. In particular, this can ensure the substitution of signal molecules and/or the build up of signal molecule gradients, which is of importance for cell cultivation. It can also help to ensure that the support structure does not constitute, or constitutes only a slight, obstacle to the formation or attachment of an extracellular matrix. It is an additional achievable advantage that the support structure has similar mechanical properties to the target tissue. The invention makes it possible for a tissue cultivated with the support structure according to the invention not to differ, or to differ less, in terms of its fundamental properties from a tissue in which no cellulose is present.

It is an achievable advantage of the present invention that the support structure can be produced by means of a mould.

In particular, a structure adapted to a specific purpose can be planned or modelled on natural examples.

It is an aspect of the process according to the invention for the production of a support structure and of the hollow mould according to the invention that it makes use of the "broken mould" principle.

It is an achievable object of the process according to the invention for the production of a support structure and of the hollow mould according to the invention that undercuts no longer represent an obstacle during demoulding. Accordingly, it is possible in particular for even hollow moulds of complex shape to be used in a simple manner. In particular, it is an achievable advantage that even support structures of complex shape, in particular those having undercuts, can be produced in a simple manner.

The invention can be used, for example, to cultivate different cell types in vitro, individually or together, in such a manner as to form therefrom a larger tissue unit, which can be studied over prolonged periods of time. The process according to the invention and the support structures according to the invention are suitable in particular for the three-dimensional cultivation of cells, for example mammalian cells. The cultivation process and the support structures can also be used for the preparation and/or regeneration of living tissue, in particular of human organs or tissue. The invention can be used for recreating extracellular structures of natural tissue, which are subsequently populated with the cell types that occur naturally in those tissues.

After they have been cultivated in vitro, the cells or tissue can be implanted, for example, into a living organism, in particular into a mammal, in particular humans. However, it is also conceivable to implant the support structure without previously populating it, in order to permit in vivo population. The support structure can initiate the self-organisation of the cells in vivo by providing a structure. In that manner, the invention for the first time offers the possibility of specifically and stably restructuring a (soft) tissue in vivo.

Composition and Further Development of the Solution According to the Invention

The support structure preferably comprises crystalline cellulose. The support structure preferably consists substantially of water and crystalline cellulose, particularly preferably microcrystalline cellulose, as is formed by the bacterium *Acetobacter xylinum*. The preferred material comprises less than 1.0 percent crystalline cellulose. In the preferred material, the water is bonded partially and with varying degrees of strength to the microcrystalline cellulose. Crystalline cellulose has proved to be particularly tissue-friendly in experiments. The cellulose-forming organisms are preferably bacteria, particularly preferably bacteria of the strain *Acetobacter xylinum*. It is conceivable for other cellulose-forming microorganisms also to be used, such as, for example, suitable strains of *Agrobacterium, Rhizobium, Sarcina, Pseudomonas, Achromobacter, Aerobacter* and *Zooglea*. Because the genes of the cellulose-synthesising enzyme complexes of *Acetobacter xylinum* are known, they could also be introduced into other microorganisms, such as, for example, *Escherichia coli*, using known molecular-biological processes, as a result of which these organisms could also synthesise cellulose. Support structures of combinations of crystalline cellulose and other materials are also conceivable, however, for example with synthetic resorbable or non-resorbable polymers, for example those disclosed in International Published Patent Application WO 2006/096791. The totality of the relevant content of the above-mentioned specification is incorporated by reference in the present disclosure. It is also conceivable for the support structure to comprise collagen, as disclosed, for example, in European Patent Specification EP 1 053 757, fibrin and/or albumin, as disclosed in International Published Patent Application WO 2006/099137 A1, or acellularised natural tissue, as disclosed, for example, in European Published Patent Application EP 1 230 930 A1. The totality of the relevant content of the above-mentioned specifications is incorporated by reference in the present disclosure. The other material is preferably enclosed substantially completely by crystalline cellulose.

A particularly preferred support structure has in its inside a plurality of voids which are separate from one another. The voids can be, for example, globular or can form tubular channels, particularly preferably spiral channels. The voids are particularly preferably connected to the outside of the support structure by openings, for example by tubular channels. It is an achievable advantage of this embodiment of the invention that cells to be cultivated, or precursors of the cells to be cultivated, are able to enter the voids from the outside through the openings. It is also conceivable for a medium, for example a nutrient medium or blood, to flow through a void in which cells have settled, in order to supply the cells with nutrients and oxygen or to influence the development of the cells by means of the flow. The openings can also be used to enable a product of the cells, for example keratin, to pass to the outside.

A preferred support structure comprises at least one tubular void which branches in at least one location. Particularly preferably, at least some of the branches converge again at a different location. Particularly preferably, the support structure comprises a system of branching and reconverging tubes, similar to a vascular system. The void is preferably connected to the outside of the support structure in at least two locations by an opening. Particularly preferably, the locations at which the void branches and the locations at which the branches converge again are arranged between the two locations at which the void is connected to the outside of the support structure by openings. It is an achievable advantage of this embodiment of the invention that liquids, for example nutrient solutions or blood, can be passed through the branches, the liquid being introduced at the first of the two locations and removed again at the second.

In the process according to the invention for the production of a support structure of cellulose, the cellulose is preferably crystalline cellulose. The cellulose-forming organisms are preferably bacteria, particularly preferably bacteria of the strain *Acetobacter xylinum*. Various nutrient media are described for the cultivation of *Acetobacter xylinum*. A suitable medium that is frequently used is Schramm and Hestrin's medium, which is described in Biochemical Journal 58 of 1954, p. 345-352. The totality of the relevant content of the above-mentioned article is incorporated by reference in the present disclosure. A disadvantage of this medium may be that it is not precisely defined, because it contains yeast extract and peptone.

A fully synthetic medium is preferred for carrying out the present invention, as described, for example, by Formg et al. in Applied and Environmental Biology of 1989, Vol. 55, No. 5, p. 1317-1319. The totality of the relevant content of the above-mentioned article is incorporated by reference in the present disclosure. A disadvantage of this medium may be slightly slower growth of the bacteria.

It is also conceivable to use so-called Kombucha mushroom tea for carrying out the invention. As well as comprising *Acetobacter xylinum*, this culture comprises many other organisms living in symbiosis, such as yeasts and bacteria, and can be supported by a medium consisting solely of black tea and sucrose (100 g/l).

In the production process according to the invention, the irreversible deformation can take place, for example, by plastic deformation, by a loss of form by breakage or by at least partial transition into a liquid or gaseous state of aggregation, preferably by melting or evaporation. However, embodiments of the invention are also conceivable in which deformation is effected by chemical treatment, for example by means of a solvent, or by mechanical treatment, for example by ultrasound. The part of the hollow mould that is irreversibly deformed in the demoulding step is preferably adjacent, before the deformation, to the cellulose formed in the hollow mould. The step of demoulding the hollow mould is preferably carried out after the support structure has filled the hollow mould completely.

In a preferred embodiment of the production process according to the invention, the hollow mould comprises an outer mould and at least one mould core. It is an achievable advantage of this embodiment of the invention that a support structure with voids can be formed using the hollow mould. A mould core is preferably part of the hollow mould which is irreversibly deformed on demoulding. It is an aspect of this embodiment of the invention that it does not make use of the concept known from the prior art of a mould core that can be withdrawn on demoulding. The hollow mould can also comprise more than one mould core. In the case of a plurality of mould cores, preferably at least one mould core, particularly preferably all the mould cores, are irreversibly deformed in the demoulding step. During demoulding, the mould core is preferably treated at least partially with heat. The demoulding step preferably comprises at least partial melting of the mould core. It is possible for the whole mould core or only specific parts thereof to melt. For example, it is conceivable for the mould core to comprise one or more non-meltable constituents which are joined to, preferably held together by, one or more meltable constituents.

In a preferred embodiment of the invention, the melting point of the part of the hollow mould that melts in the demoulding step is above 28° C., particularly preferably at or above 30° C., particularly preferably at or above 60° C. It is an achievable advantage of this embodiment of the invention that the mould core remains stable during the cultivation of the cellulose. In a preferred embodiment of the invention, the melting point of the part of the hollow mould that melts in the demoulding step is below 100° C., particularly preferably below 80° C., particularly preferably 62° C. It is an achievable advantage of this embodiment of the invention that the cellulose support structure is not damaged when the mould core is melted.

During demoulding of the hollow mould, the mould core is preferably removed substantially, particularly preferably quantitatively, that is to say without a residue.

The part of the mould core that melts during demoulding is preferably substantially hydrophobic. It is an aspect of this embodiment of the invention that use is made of the fact that a hydrophobic material is repelled by the hydrophilic surface of the cellulose body. It is an achievable advantage of this embodiment of the invention that the hollow mould can be removed substantially quantitatively.

In a preferred embodiment of the invention, the part of the mould core that melts during demoulding comprises a thermoplastic material, particularly preferably a thermoplastic wax and/or polymer material. It is an achievable advantage of mould cores of thermoplastic materials that they can be produced by casting. It is a further advantage of wax and/or polymer materials that their surfaces can be smoothed simply by polishing, in order to facilitate the close attachment of the synthetic cellulose.

A preferred wax and/or polymer material comprises polyvinyl alcohol (PVA), particularly preferably in an amount of more than 1%, particularly preferably more than 50%. In a particularly preferred embodiment of the invention, the wax and/or polymer material consists substantially completely of polyvinyl alcohol. It is an achievable advantage of this embodiment of the invention that it is possible to avoid leaving behind toxic residues after removal of the hollow mould, because polyvinyl alcohol is non-toxic.

Another preferred wax and/or polymer material is so-called "summer wax", which is known from dentistry. It is an achievable advantage of this embodiment of the invention that the material is so mechanically stable that even filigree structures are retained. It is an achievable advantage of this embodiment of the invention that it is possible to avoid leaving behind toxic residues after removal of the hollow mould, because summer wax is non-toxic.

In a preferred production process, the mould core has at least one strand which branches in at least one location. At least some of the branches preferably converge again in a different location. It is an achievable advantage of this embodiment of the invention that a system of branching and reconverging tubes, similar to a vascular system, can be created in the support structure. The mould core is preferably composed of wax filaments, preferably of summer wax, as are known from dentistry. The filaments are preferably fused to one another.

A preferred support structure produced by the production process has at least one opening through which the deformed, preferably melted mould core or its residues can leave the inside of the support structure. The preferred support structure has in its inside at least one undercut, preferably such that a rigid mould core that completely fills the inside of the hollow body cannot be removed from the hollow body without deforming the mould core. The support structure preferably has in its inside at least one void which is accessible from the outside only by passing through a narrow portion, the cross-section of which is smaller than the cross-section of the void.

BRIEF DESCRIPTION OF THE DRAWINGS

The invention is explained in further detail hereinbelow with reference to diagrammatic drawings and embodiments. In the drawings.

DESCRIPTION WITH REFERENCE TO AN EMBODIMENT

Figure 1:
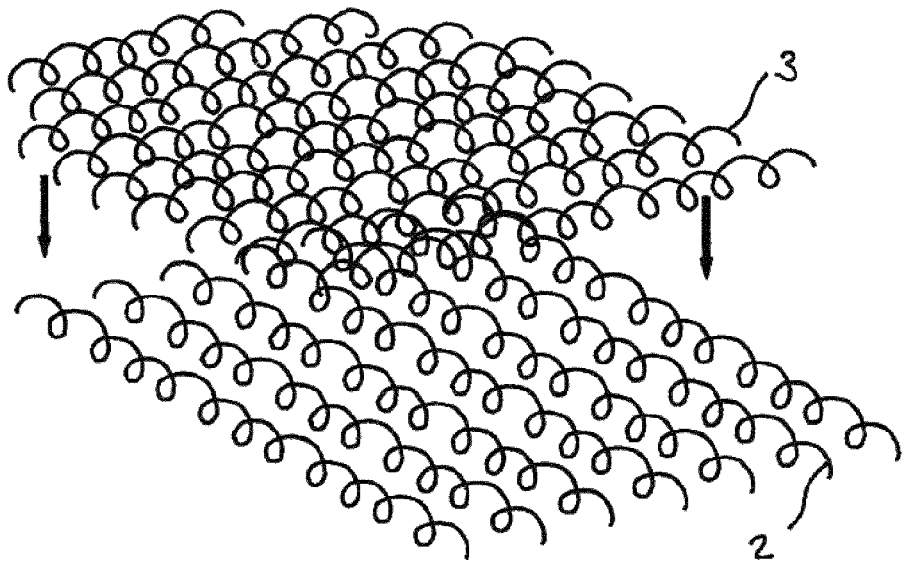
FIG. 1: shows a first perspective view, in diagrammatic form, of a first embodiment of a mould core for the process according to the invention for the production of a support structure.
Figure 2:
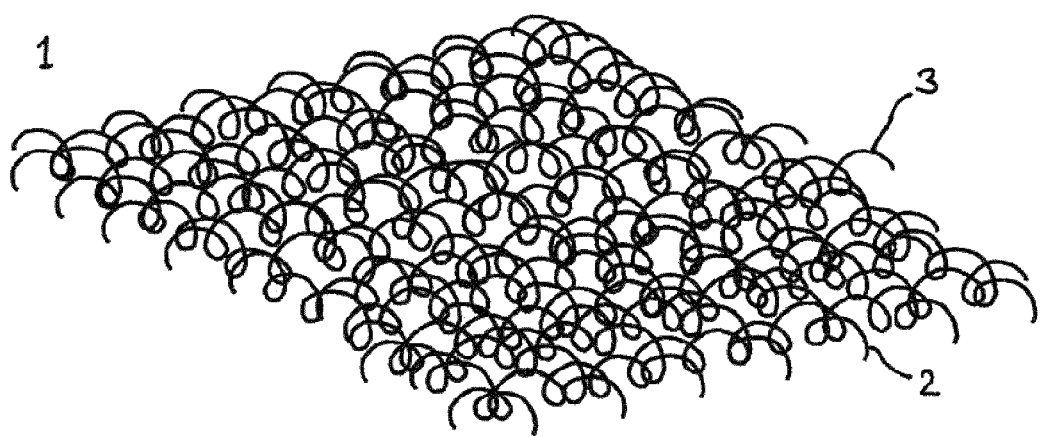
FIG. 2: shows a second perspective view, in diagrammatic form, of the first embodiment of a mould core for the production process according to the invention.

FIGS. 1 and 2 show an arrangement 1 for the production of a cellulose support structure of suitable mould cores 2, 3 of helically wound wax filaments, for example of summer wax. The filaments are arranged in two planes, the filaments in each plane being oriented substantially parallel to one another. The wax filaments 2 in the first plane are oriented at an angle of, for example, 90° relative to those 3 of the second plane. The two planes lie directly above one another and are shown offset in FIG. 1 only for reasons of clarity. Filaments 2 of the first plane touch filaments 3 of the second plane in some locations. The spiral wax filaments can be produced in an extrusion process, for example. The arrangement 1 is suitable for producing a support structure of cellulose which has helical voids, some of the helical voids being connected to others by openings.

Figure 3:
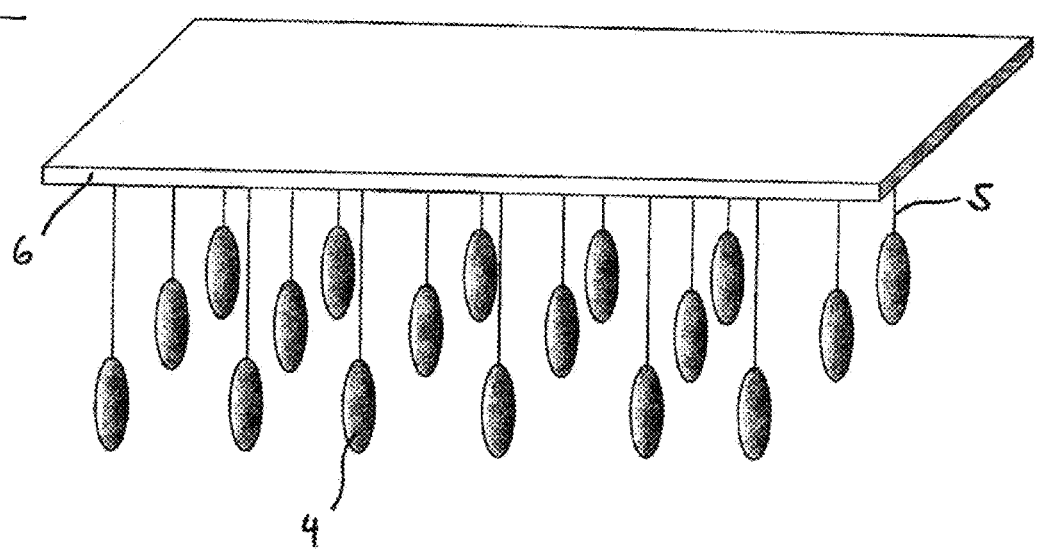
FIG. 3: shows a perspective view, in diagrammatic form, of a second embodiment of a mould core for the production process according to the invention.

A second embodiment of a mould core for the process according to the invention for the production of a support structure is shown in FIG. 3. Globular wax drops 4, for example having a diameter of approximately from 50 to 100 μm, are suspended on thin threads, for example wax threads or steel wires 5, which are anchored to a body 6, for example to a plate 6. The arrangement is suitable for the production of a support structure having a plurality of globular voids, which are produced by the wax drops 4, the voids being connected to the outside of the support structure by narrow channels, which are produced by the wires 5.

Figure 4:
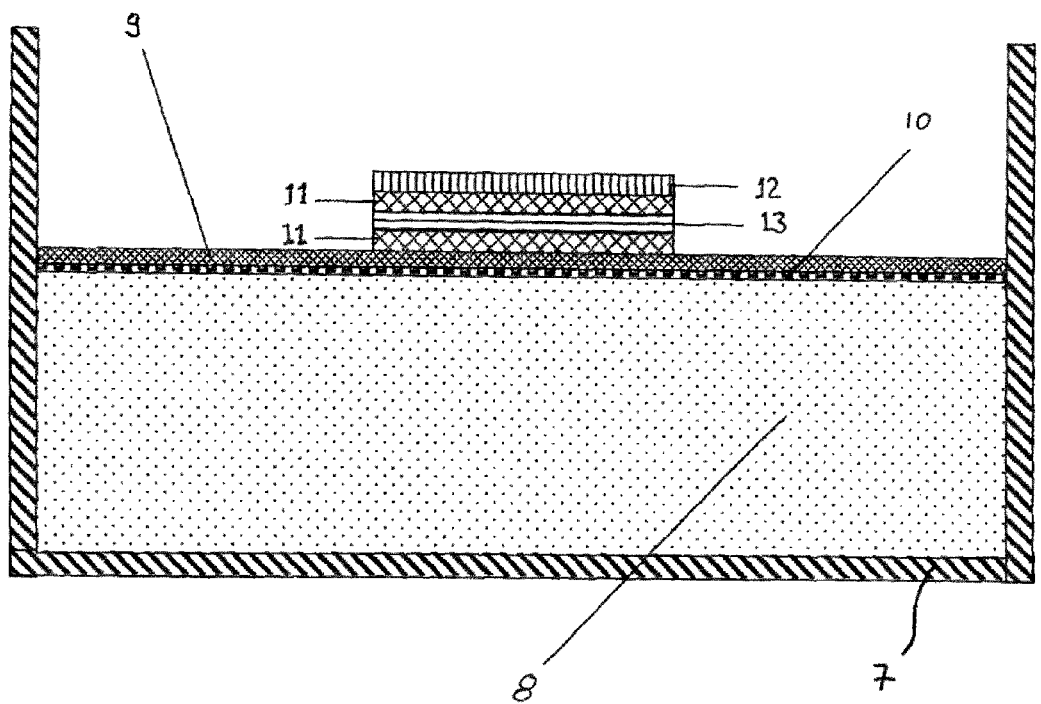
FIG. 4: shows a cross-sectional view, in diagrammatic form, of an arrangement for carrying out the production process according to the invention.

An embodiment of an arrangement for carrying out the process according to the invention for the production of a support structure is shown in diagrammatic form in FIG. 4. A sterile vessel 7 is filled with a sterile nutrient solution 8 consisting of 20 g of glucose, 5 g of yeast extract, 5 g of bactopeptone, 2.7 g of sodium phosphate and 1.15 q of citric acid monohydrate, pH 6.0, and inoculated with a 3-day-old preliminary culture of *Acetobacter xylinum* (e.g. *Gluconacetobacter xylinus*, DSM No. 2325, DSZM Brunswick). When, after about 7 days, a layer 9 of cellulose having a thickness of about 3 mm has formed on the surface of the liquid, the layer 9 is supported by a net 10 of Teflon (ePTFE expanded polytetrafluoroethylene, e.g. GLIDE dental floss, W.L. Gore and Associates Inc.), which is clamped in a glass frame carried by glass supports. A hollow mould having a plurality of planes with mould cores 11, 12, 13 of summer wax is placed on the cellulose surface 9 supported by the net 10 and cultivated at 28° C. in an incubator.

It generally takes from 2 to 3 weeks for the hollow mould to become populated with the bacteria and filled completely with cellulose. During this time it must be ensured that medium 8 that has been consumed or has evaporated is replaced, if necessary. When the hollow mould is filled completely with cellulose, the support structure is removed and then heated to about 65° C. so that the mould cores melt and leave behind voids in the support structure. Heating at the same time serves to sterilise the support structure.

Figure 5:
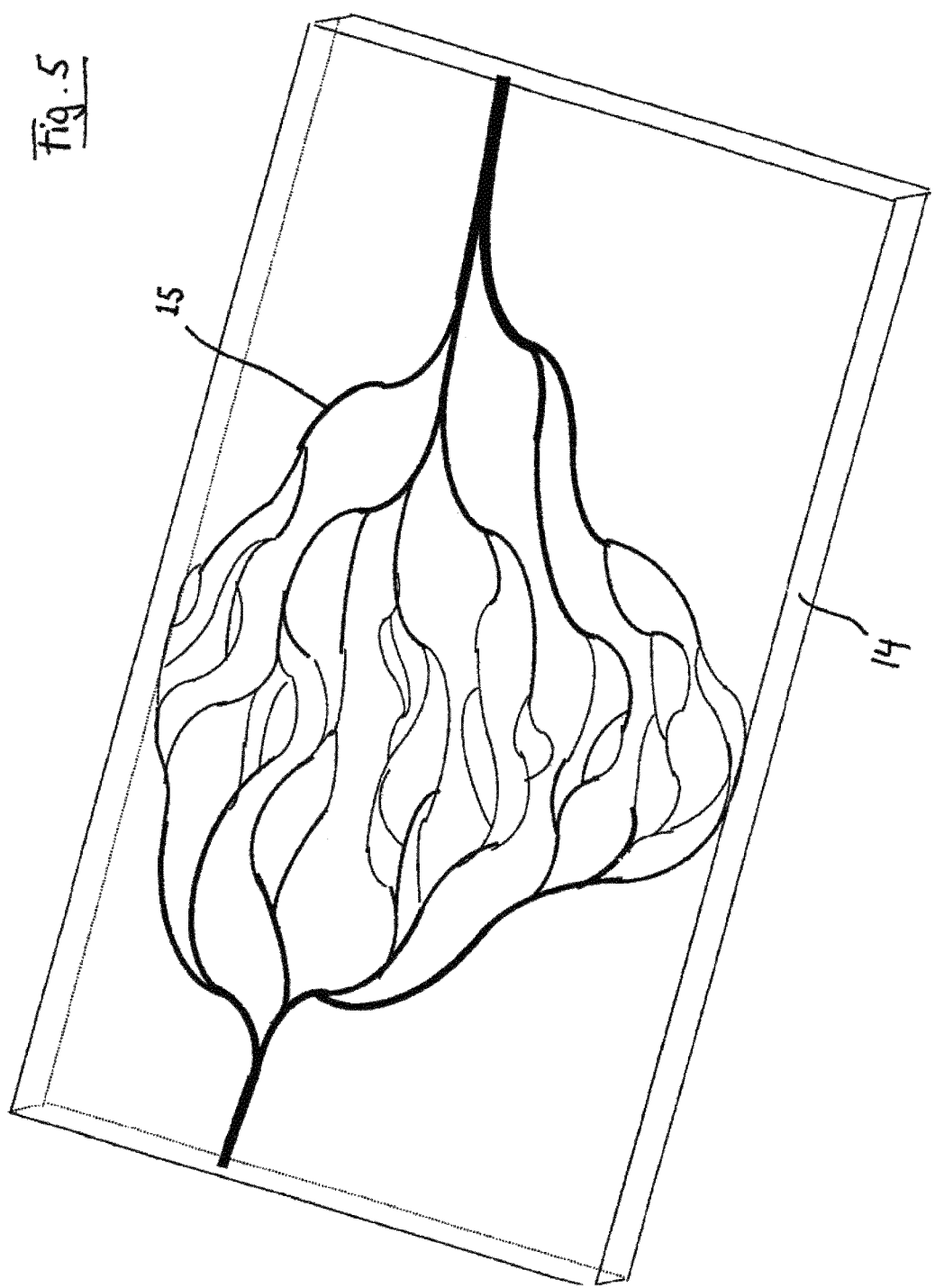
FIG. 5: shows a perspective view, in diagrammatic form, of an embodiment of a support structure according to the invention.

FIG. 5 shows an example of a support structure 14 which has been produced by means of a mould core formed by wax filaments which have been fused together to form a network 15 of branching and reconverging strands. The wax filaments used are filaments of summer wax, which are commercially available in the dental field. When the cellulose has completely filled the hollow mould having the interwoven wax filaments 15 as mould core, the support structure 14 is removed and heated to 65° C. in order to melt the interwoven wax filaments. The wax can thus be removed substantially completely from the support structure 14. There remains a void of branching and reconverging tubes, similar to a vascular system. The void is connected to the outside of the support structure in two locations by an opening. The locations at which the void branches and the locations at which the branches converge again are arranged between the two locations at which the void is connected to the outside of the support structure 14 by openings.

The invention claimed is:

1. A process for producing a support structure comprising crystalline cellulose for the cultivation of living cells, comprising the steps of:

preparing a hollow mould, wherein the hollow mould comprises an outer mould and at least one mould core, the outer mould and the at least one mould core forming an interior space;

preparing a vessel containing a nutrient solution;

cultivating cellulose-producing bacteria inside the vessel so that a layer of microbial cellulose forms on to of the nutrient solution;

placing the hollow mould on top of the layer of microbial cellulose;

letting the layer of microbial cellulose grow further into the interior space of the hollow mould so that the layer of microbial cellulose fills the interior space of the hollow mould and covers the at least one mould core; and demoulding the hollow mould, wherein at least part of the mould core is irreversibly deformed in the step of demoulding the hollow mould, thereby producing the support structure.

2. The process according to claim 1, wherein the mould core is substantially removed in the step of demoulding the hollow mould.

3. The process according to claim 1, wherein the demoulding step comprises the step of at least partially melting the mould core.

4. The process according to claim 3, wherein the melting point of the part of the mould core that melts in the demoulding step is above 28° C.

5. The process according to claim 3, wherein the part of the mould core that melts during demoulding is substantially hydrophobic.

6. The process according to claim 3, wherein the part of the mould core that melts during demoulding comprises a thermoplastic wax and/or polymer material.

7. The process according to claim 1, wherein the mould core has at least one strand that branches in at least one location.

* * * * *

UNITED STATES PATENT AND TRADEMARK OFFICE
CERTIFICATE OF CORRECTION

| | | |
|---|---|---|
| PATENT NO. | : 8,993,324 B2 | Page 1 of 1 |
| APPLICATION NO. | : 12/526752 | |
| DATED | : March 31, 2015 | |
| INVENTOR(S) | : Bertholdt | |

It is certified that error appears in the above-identified patent and that said Letters Patent is hereby corrected as shown below:

In the claims,

Claim 1 – Col. 10 Line 7 – delete "on to of the" and replace with --on top of the--

Signed and Sealed this
Twenty-first Day of July, 2015

Michelle K. Lee
*Director of the United States Patent and Trademark Office*